United States Patent [19]

Dive et al.

[11] Patent Number: 5,776,903
[45] Date of Patent: Jul. 7, 1998

[54] PEPTIDE DERIVATIVES USABLE AS ZINC ENDOPEPTIDASE 24-15 INHIBITORS

[75] Inventors: Vincent Dive. Vincennes, France; Jiri Jiracek. Prague, Czechoslovakia; Athanasios Yiotakis. Athens, Greece

[73] Assignee: Commissariat A l'Energie Atomique. Paris, France

[21] Appl. No.: 590,483

[22] Filed: Jan. 24, 1996

[30] Foreign Application Priority Data

Feb. 6, 1995 [FR] France .................. 95 01328

[51] Int. Cl.⁶ .................. A61K 38/07; C07K 5/10
[52] U.S. Cl. .................. 514/18; 514/7; 530/330; 530/304; 530/302; 530/300; 435/212
[58] Field of Search .................. 514/7, 18; 530/330, 530/304, 302, 300; 435/212

[56] References Cited

U.S. PATENT DOCUMENTS

| 5,389,612 | 2/1995 | Dive et al. | 514/7 |
| 5,500,414 | 3/1996 | Dive et al. | 514/8 |

FOREIGN PATENT DOCUMENTS

| 0 276 436 | 8/1988 | European Pat. Off. |
| WO 93/14112 | 7/1993 | WIPO |

OTHER PUBLICATIONS

Oorlowski et al, Biochem. J., vol. 261, pp. 951–958, (1989).

Barelli, et al., "Potent Inhibition of Endopeptidase 24.16 and Endopeptidase 24.15 by the Phosphonamide Peptide N-(phenylethylphosphonyl)-Gly-L-Pro-L-aminohexanoic Acid," *Biochemical Journal*—vol. 287(2) pp. 621–625 (1992).

Knight et al., "Thimet Oligopetidase Specificity: Evidence of Preferential Cleavage Near the C-Terminus and Product Inhibition From Kinetic Analysis of Peptide Hydrolysis," *Biochemical Journal*—vol. 308(1), pp. 145–150 (1995).

Bruno, et al., Phosphorus–Containing Peptides a Mixed Inhibitors of Endopeptidase 3.4.24.15 and 3.4.24.16: Effect on Neurotensin Degradation in vitro and in vivo., *British Journal of Pharmacology*—vol. 115(6), pp. 1053–1063 (1995).

Doulot, et al., "Synthesis and Analgesic Effects of N-|3 |(Hydroxyamino)carbonyl|-1-oxo-2(R)-benzylpropyl| -L-isoleucyl-L-leucine, a New Potent Inhibitor of Multiple Neurotensin/Neuromedin N Degrading Enzymes", *Journal of Medicinal Chemistry*—vol. 36(10), pp. 1369–1379 (1993).

*Primary Examiner*—Ponnathapura Achutamurthy
*Assistant Examiner*—T. D. Wessendorf
*Attorney, Agent, or Firm*—Burns, Doane, Swecker & Mathis, LLP

[57] ABSTRACT

Peptide derivatives usable as zinc endopeptidase 24–15 inhibitors.

These peptide derivatives have the following amino acid sequence:

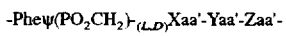

in which $\psi(PO_2CH_2)$ indicates that the peptide bond (CONH) has been replaced by the phosphine bond $(PO_2CH_2)$. Xaa' and Zaa', which can be the same or different, in each case represent a natural amino acid or an amino pseudo-acid and Yaa' represents Arg or Lys.

As examples of such derivatives, reference can be made to those of formula:

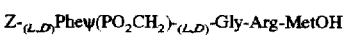

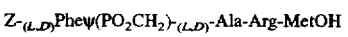

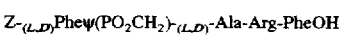

with Z representing the benzyloxycarbonyl group.

6 Claims, 2 Drawing Sheets

PEPTIDE DERIVATIVES USABLE AS ZINC ENDOPEPTIDASE 24-15 INHIBITORS

The present invention relates to novel peptide derivatives usable as inhibitors of zinc endopeptidase EC.3.4.24-15.

More specifically, it relates to peptide derivatives, which are powerful and selective inhibitors of the endopeptidase 24-15, whilst being inactive with respect to other zinc peptidases such as endopeptidase 24-16, the hypertension conversion enzyme, endopeptidase 24-11, aminopeptidases M and L and carboxypeptidases A and B.

It is of considerable pharmacological importance to obtain zinc protease inhibitors. Thus, as a result of the function they fulfil in mammals in the metabolism of proteins and peptides, numerous zinc metalloproteases are involved in important physiological functions and can be the origin of various pathologies. With respect to the central nervous system and also more peripheral systems, a certain number of zinc endopeptidases (endopeptidases 24-11, 24-15 and 24-16) are involved in the deterioration or maturation of numerous neuropeptides. With respect to the cardiovascular system, the hypertension and endothelin conversion enzymes play an essential part in regulating the arterial pressure. There are also zinc metalloproteases, whose activity is associated with ageing illnesses and diseases and the development of cancerous metastases (collagenase, elastase, gelatinase, stromelysine). In certain cases such metalloproteases have been identified as being closely associated with the virulence of certain microorganisms (botulism and tetanus oxines, cholera hemagglutine, pseudomonas aeruginosa, peridontal diseases due to collagenolytic bacteria).

It would therefore be of interest to have specific inhibitors of these proteases for therapeutic purposes.

Various groups throughout the world have acquired an interest in such a problem and have developed a rational approach for synthesizing such inhibitors. This is based on a fundamental property of zinc metalloproteases, namely the presence in their active site of a zinc atom participating in the catalysis of the hydrolysis of the peptide bond.

Globally this strategy consists of synthesizing analogous peptides with substrates of such proteases, but in which replacement takes place of the peptide bond (CO—NH) cleaved by these proteases by a chemical group having on the one hand good structural and electronic analogies with the peptide bond in the transition state and on the other hand able to strongly interact with the zinc atom present in the active site of said proteases.

FIGS. 1 to 3 illustrate the fundamental state of a peptide substrate of said enzymes and then its transition state (FIG. 2) and the transition state (FIG. 3) of an inhibitor constituted by an analog of the peptide substrate in which the CO—NH bond cleaved by the enzyme has been replaced by a $PO_2$-X bond with X representing NH, O or $CH_2$.

In FIG. 1, $R^1$, $R^2$, $R^3$, $R^{1'}$, $R^{2'}$ and $R^{3'}$ represent the side chains of amino acids on either side of the peptide or phosphine bond involved in the reaction with the enzyme.

Thus, for such inhibitors, use has hitherto been made of chemical groups of the phosphonamide (X=NH), phosphone (X=O) or phosphine ($X=CH_2$) type, which have good structural and electronic analogies with the peptide bond in the transition state.

The similarity of these inhibitors with substrates in the transition state generally gives said molecules exceptional affinities.

The introduction of a phosphonamide bond into substrates has been described in FR-A-2 654 430 and has proved to be very effective for arriving at powerful inhibitors of certain zinc proteases. However, the chemical stability of the phosphonamide bond is highly dependent on the amino acid sequences surrounding said bond and unfortunately, for certain sequences, there is a very rapid hydrolysis of the phosphonamide bond.

The use made of a phosphonate-type bond has been described by Kaplan et al in Biochemistry 30, 1991, pp 8165–8170 and has made it possible to obtain in this specific case of the carboxypeptidase A the most powerful synthetic inhibitor hitherto reported for an enzyme (inhibition constant $K_i=10^{-5}M$).

Inhibitors containing a phosphine bond ($X=CH_2$) have been described in FR-A-2 676 059 and have proved to be very effective in the case of bacterial collagenases. EP-A-565 450 describes inhibitors containing a phosphonamide bond (X=NH) very effective with respect to the endopeptidase 24.15, but also very good inhibitors of endopeptidase 24.16.

The present invention has developed novel peptide derivatives having a phosphine bond and which are powerful and selective as inhibitors of endopeptidase 24-15. These products are in particular inactive with respect to other proteases and in particular the endopeptidase 24-16, the hypertension conversion enzyme, endopeptidase 24-11, aminopeptidases M and L and carboxypeptidases A and B. These derivatives are much more chemically stable than phosphonamide peptides.

According to the invention, these novel peptide derivatives have the following amino acid sequence:

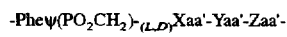

in which $\psi(PO_2CH_2)$ indicates that the peptide bond (CONH) has been replaced by the phosphine bond ($PO_2CH_2$), Xaa' and Zaa', which can be the same or different, in each case represent a natural amino acid or an amino pseudo-acid and Yaa' represents Arg or Lys.

In this sequence the group $PO_2CH_2$ is in the form $PO_2^-$, as can be gathered from FIG. 3. Thus, it is associated with a counterion such as $K^+$, $Na^+$ or any other metal which is acceptable from the pharmacological standpoint. The nature of the counterion is unimportant, because in water the charged groups are dissociated.

According to an embodiment of the invention, these peptide derivatives comply with one of the formulas:

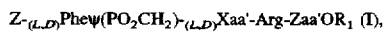

and

in which

Z represents a conventional peptide synthesis protective group, such as the acetyl or benzyloxycarbonyl group, $\psi(PO_2CH_2)$ indicates that the peptide bond (CO—NH) has been replaced by the phosphine bond ($PO_2CH_2$), Xaa' and Zaa', which can be the same or different, in each case represent a natural amino acid or an amino pseudo-acid and $R^1$ represents a hydrogen atom, $NH_4^+$ or a pharmaceutically acceptable metal.

In the aforementioned formulas (I) and (II), the amino acids used for Xaa' and Zaa' can be natural amino acids or amino pseudo-acids.

The natural amino acids can be chosen from among alanine, arginine, asparagine, aspartic acid, cysteine, glutamine, glutamic acid, glycine, histidine, isoleucine, leucine, norleucine, lysine, methionine, phenylalanine, proline, hydroxyproline, serine, threonine, tryptophan, tyrosine, valine, nitrophenyl alanine, homoarginine, thiazolidine and dehydroproline.

An amino pseudo-acid can be defined as an amino acid in which the either amino or carbonyl function has been replaced by another chemical group.

The metal used for $R^1$ can be an alkali metal such as sodium, potassium or lithium.

Moreover, as can be gathered from the formula, the amino acids Phe and Xaa' can be in L or D form. The peptide derivative of formula (I) or (II) can be constituted by a mixture of 4 diastereoisomers or by one only of said isomers.

Preferably, in the aforementioned formulas (I) and (II), Xaa' represents Gly, Ala or Leu, because the presence of such an amino acid in the vicinity of the phosphine bond makes it possible to obtain very good inhibitors.

These peptide derivatives are different from those described in EP-A-565 450 for which the Gly-Pro linkage (or Pro analog) or Ala-Pro linkage (or Pro analog) is always present in the vicinity of the phosphine bond. In the invention, the proline group (hydroxyproline, thiazolidine or dehydroproline) has been replaced by an arginine or lysine group making it possible to attain a very high selectivity for endopeptidase 24-15 with respect to endopeptidase 24-16.

Thus, in these derivatives, the choice of arginine (formula I) or lysine (formula II) makes it possible to achieve the desired specificity.

Thus, any peptide containing a phosphine bond can potentially be an inhibitor of different proteases belonging to the family of zinc metalloproteases. However, apart from interactions of the phosphine bond with the zinc atom of the active site, the affinity of the peptide is also dependent on the interactions between the amino acids on either side of the phosphine unit ($R^1$, $R^2$, $R^3$, $R^{1'}$, $R^{2'}$ and $R^{3'}$ in FIG. 3) and the different subsites ($S^1$, $S^2$, $S^3$, $S^{1'}$, $S^{2'}$ and $S^{3'}$ of FIG. 1) of the active site of the protease.

According to the invention, it has been found that in the case of endopeptidase 24-15, the presence of arginine or lysine in the $R^{2'}$-position has given the peptide a high affinity for the subsites of endopeptidase 24-15 and little affinity for the subsites of other proteases.

According to the invention, the amino acid representing Zaa' is also very important, because its choice makes it possible to optimize the interaction of the inhibitor with endopeptidase 24-15 and is unfavourable to its interaction with respect to endopeptidase 24-16 and other proteases. Preferably, according to the invention, Zaa' represents Met, Nle, Ala or Phe.

In the case of derivatives of formula II, good results are also obtained when Zaa' represents Leu or Ile.

In the case of the derivative of formula I, better results are obtained with regards to the power and selectivity of the inhibitor, when Xaa' represents Ala and Zaa' Met.

In the case of derivatives of formula II, very good results are obtained when Xaa' represents Ala and Zaa' Met or Phe.

Thus, according to the invention, powerful and selective inhibitors of endopeptidase 25-15 of the mammal or thimet peptidase are available, which are also very poor inhibitors of endopeptidase 24-16. This is a very important result, because peptidases 24-15 and 24-16 have very close specificities and hitherto all that was available consisted of mixed inhibitors of said two peptidases, as described by H. Barelli et al in Biochem. J., 1992, 287, pp 621–625 and EP-A-565 450.

The peptide derivatives according to the invention can be prepared by conventional processes, like that described in FR-A-2 676 059.

However, preference is given to the preparation of derivatives of formula (I) or (II) by solid phase synthesis processes on the basis of synthones of formula:

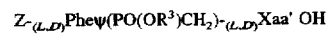
Z-$_{(L,D)}$Pheψ(PO(OR$^3$)CH$_2$)-$_{(L,D)}$Xaa' OH in which Z, Phe, ψ and Xaa' have the meanings given hereinbefore and $R^3$ represents the adamantyl group.

The invention also relates to a process for the preparation of a peptide derivative complying with formulas (I) or (II) and which consists of coupling the dipeptide fixed to a solid phase of formula: NH$_2$-Arg-Zaa'R$_2$ or NH$_2$-Lys-Zaa'R$_2$, in which Zaa' has the meaning given hereinbefore and R$_2$ is the solid phase, with the synthone of formula:

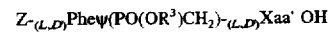
Z-$_{(L,D)}$Pheψ(PO(OR$^3$)CH$_2$)-$_{(L,D)}$Xaa' OH in which Z, ψ, Xaa' and $R^3$ are as defined hereinbefore, followed by the separation of the peptide derivative of formula:

Z-$_{(L,D)}$Pheψ(PO(OR$^3$)CH$_2$)-$_{(L,D)}$Xaa'Arg-Zaa'R$^2$ or

Z-$_{(L,D)}$Pheψ(PO(OR$^3$)CH$_2$)-$_{(L,D)}$XaaLys-Zaa'R$^2$ from the solid phase $R^2$ and eliminating the $R^3$ group by an acid treatment.

In the process described hereinbefore, the different stages are performed by conventional procedures using the reagents and solvents generally used in peptide chemistry.

The invention also relates to a pharmaceutical composition incorporating an endopeptidase 24-15 inhibitor, characterized in that said inhibitor is a peptide derivative incorporating the following amino acid sequence:

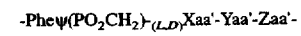
-Pheψ(PO$_2$CH$_2$)-$_{(L,D)}$Xaa'-Yaa'-Zaa'- or complying with one of the aforementioned formulas (I) and (II).

These inhibitors have the possibility of in vivo blocking the degradation of numerous biological peptides in humans (somatostatine, bradykinine, angiotensin, neurotensin, substance P, dynorphine, VIP), so as to be able to potentialize the biological effects of these different peptides. The in vivo use of these products consequently opens up significant pharmacological applications involving these biological peptides and their degradation by endopeptidase 24-15. The same peptidase has also been recently implicated in Alzheimer's disease and in the maturation stages of ras proteins, which are key proteins in the development of numerous forms of cancer. It should be noted that for similar products, namely phosphorus pseudopeptidases, tests have demonstrated that these molecules in vivo in the dog were effectively able to inhibit the degradation of neurotensin for very low inhibitor concentrations, as described by Barelli, H; Fox-Threlkeld, J. E. T.; Dive, V.; Daniel, E. E.; Vincent, J. P. and Checler F. (1994) Br. J. Pharmacol. 112, 127.

In addition, the inhibition of endopeptidase 24-15 by the derivatives according to the invention, which are the most powerful and selective hitherto reported for this peptidase, have numerous pharmacological applications, more particularly as analgesics and for the treatment of hypothermia, arterial hypertension, cancer and Alzheimer's disease.

BRIEF DESCRIPTION OF THE DRAWINGS

Other features and advantages of the invention can be gathered from the following non-limitative description with respect to the attached drawings, wherein show.

Figure 1:
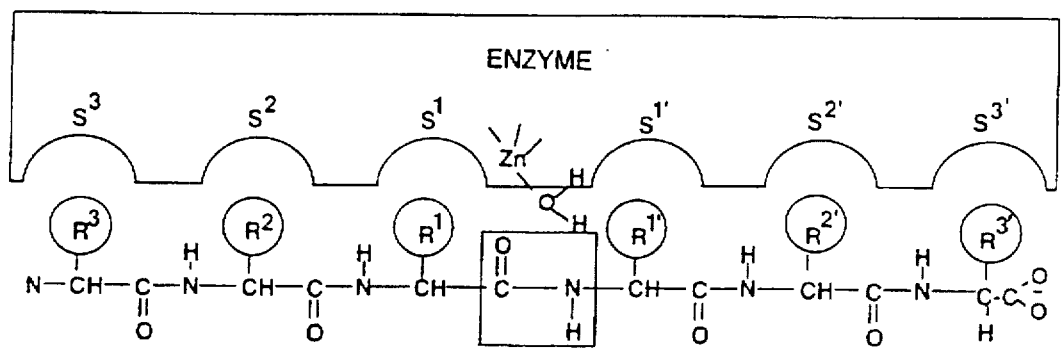
FIGS. 1 to 3, already described, the structure and interaction with an enzyme of an enzyme substrate or an inhibitor according to the invention.
Figure 2:
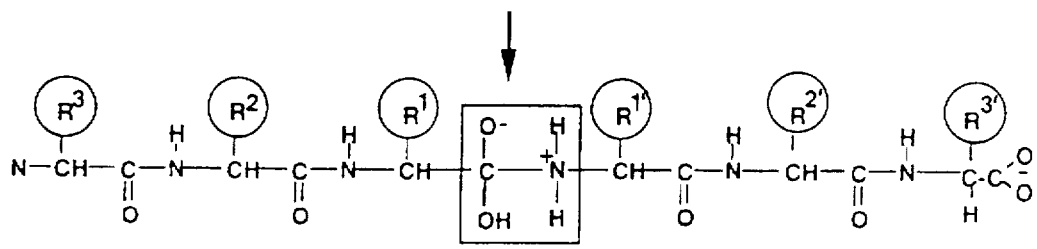
Figure 3:
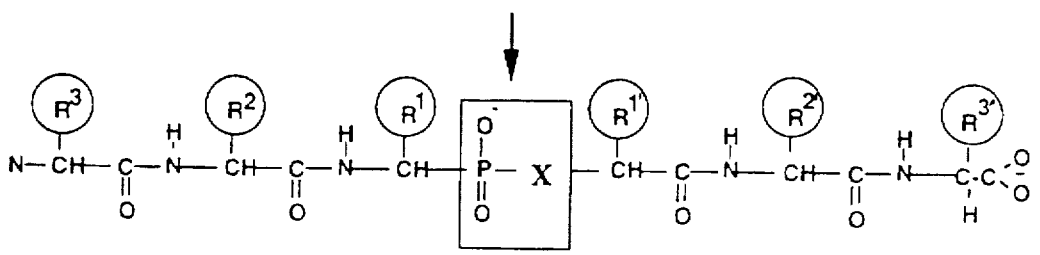

The following examples illustrate the preparation of synthones and peptide derivatives according to the invention and the properties of the peptides obtained.

EXAMPLE 1

Preparation of the synthone Z-Pheψ(PO(OR$^3$)CH$_2$) GlyOH (synthone No. 1)

a) Preparation of Z-Pheψ(PO(OR$^3$)CH$_2$)GlyO$_2$CH$_5$

The starting product for this preparation is Z-Phe ψ-(PO$_2$CH$_2$)GlyOC$_2$H$_5$, which is obtained according to example 1 (compound 4) of FR-A-2 676 059. The product is dissolved in a mixture of ethanol (20 ml) and water (5 ml). This solution is added to a 1M silver nitrate (4 ml) solution, accompanied by stirring. After 10 minutes, 20 ml of water is added and then the ethyl alcohol formed is evaporated in vacuo. The remaining aqueous phase containing the silver salt precipitate is cooled for 1 hour in a water-ice bath and then the precipitate is filtered, washed with water and dried in the presence of P$_2$O$_5$ to give a solid (0.95 g, yield 91%). This silver salt (0.95 g, 1.82 mM) is suspended in a chloroform solution (15 ml), to which is added 1-adamantyl bromide (0.473 g, 2.2 mM). The reaction mixture is refluxed for 30 minutes. The silver bromide precipitate is eliminated by filtering and then the filtered solution is concentrated by evaporation. The crude product is purified on a silica gel column using as the eluent a chloroform:isopropanol (97:3) mixture. This gives 0.66 g of pure product Z-Phe(PO(O-R$^3$) CH$^2$)GlyOC$_2$H$_5$ (yield 81%), in the form of an oil: (Rf(1) =0.63; Rf(2)=0.82; molecular weight=553.34).

b) Preparation of the synthone Z-Pheψ(PO(OR$^3$)) CH$_2$GlyOH

The product Z-Pheψ(PO(O-R$^3$)CH2)GlyOC$_2$H$_5$ obtained in a) (0.55 g, 1 mM) is dissolved in ethanol (10 ml), followed by the dropwise addition to said solution of 1 ml of 4M soda. After 90 minutes at ambient temperature, the ethanol is eliminated by evaporation in vacuo. The residual product is dissolved in water (30 ml). The solution is cooled in a water-ice bath and then acidified with 2M HCl. The solid product which precipitates is extracted with ethyl acetate, washed with water, dried on Na$_2$SO$_4$ and then concentrated to give the solid product Z-Pheψ(PO(O-R$^3$)CH$^2$)GlyOH (0.46g, yield 89%). Rf(2)=0.33; molecular weight =525.34.

EXAMPLE 2

Preparation of the synthone Z-Pheψ(PO(OR$^3$)CH$_2$) AlaOH (synthone 2)

For this preparation the operating procedure of example 1 is followed starting with the product Z-Pheψ(PO$_2$CH$_2$) AlaOC$_2$H$_5$ obtained in the same way as Z-Pheψ(PO$_2$CH$_2$) GlyOC$_2$H$_5$.

The products obtained have the following characteristics:

Z-Pheψ(PO(OR$^3$)CH$^2$)AlaOC$_2$H$_5$: Rf(1)=0.66, molecular weight= 566.35.

Z-Pheψ(PO(OR$^3$)CH$_2$)AlaOH: Rf(1)=0.42; molecular weight= 538.35.

EXAMPLE 3

Preparation of the synthone Z-Pheψ(PO(OR$^3$)CH$_2$) LeuOH (synthone 3)

The operating procedure of example 1 is used for preparing this synthone from Z-Pheψ(PO$_2$CH$_2$)LeuOC$_2$H$_5$ obtained in the same way as Z-Pheψ(PO$_2$CH$_2$) (GlyOC$_2$H$_5$.

The products obtained have the following characteristics:

Z-Pheψ(PO(OR$^3$)CH$_2$)LeuOC$_2$H$_5$: Rf(1)=0.64; molecular weight= 610.1.

Z-Pheψ(PO(OR$^3$)CH$^2$)LeuOH: Rf(1)=0.52; molecular weight 582.1.

EXAMPLE 4

Preparation of Z-Pheψ(PO$_2$CH$_2$)GlyargMetOH (peptide 1)

Figure 4:
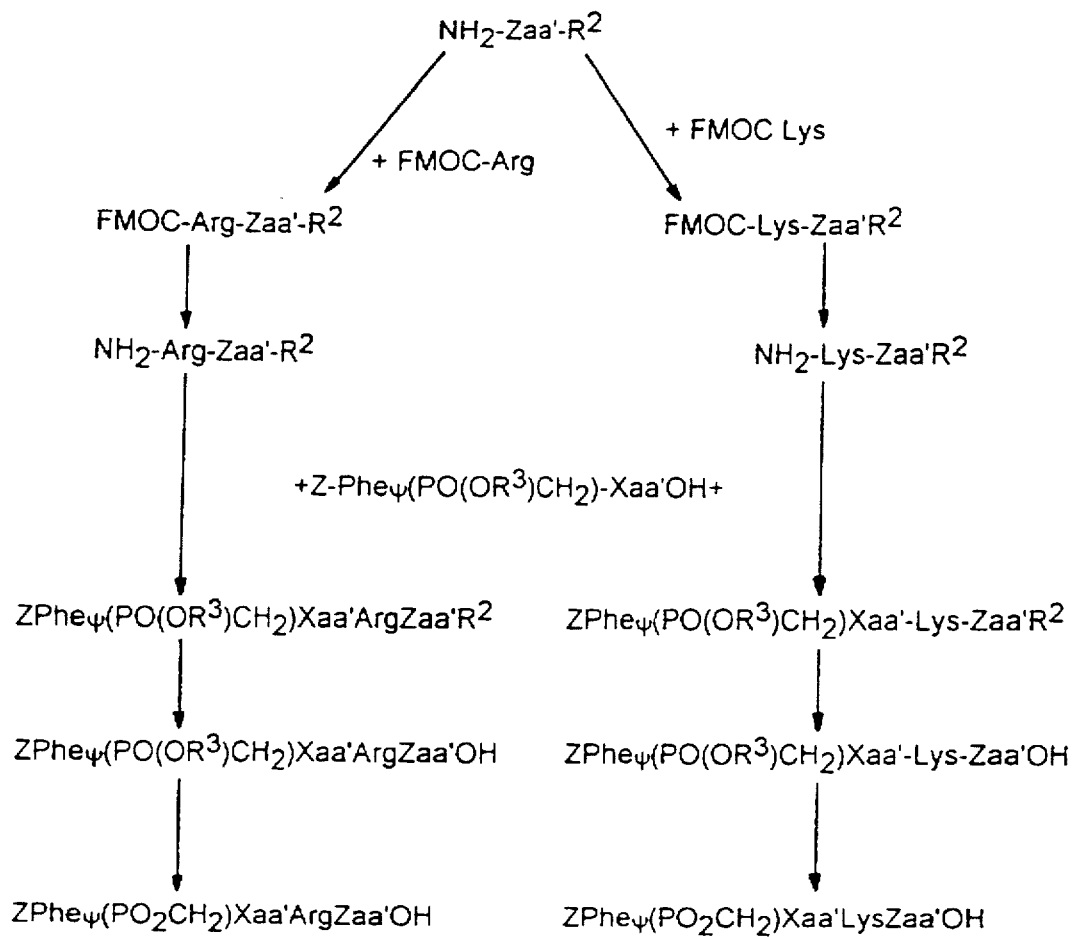
FIG. 4 The different stages of synthesizing a peptide derivative according to the invention.

For preparing this peptide use is made of a solid phase synthesis method described in FIG. 4, whilst firstly fixing to the solid phase the amino acid NH$_2$—MetOH. The solid phase is constituted by a 2-chlorotrityl resin and use is made of 50 µmole of methionine for 50 to 100 mg of dry resin.

a) Preparation of FMOC-Arg-Zaa'-R$^2$ with Zaa' representing Met, R$^2$ representing 2-chlorotrityl resin and FMOC representing 9-fluorenyl methyloxycarbonyl The resin is firstly allowed to swell with the methionine fixed above in dimethyl formamide for 15 minutes, followed by coupling with 2 to 4 equivalents of FMOC-Arg using for said coupling 2 to 4 equivalents of 2(1H benzotriazol-1-yl) 1,1,3,3-tetramethyl uronium hexafluorophosphate (HBTU), 2.5 to 5 equivalents of diisopropylamine (DIPEA) and 1 to 1.5 ml of dimethyl formamide DMF (NMP), whilst carrying out the coupling in 30 to 60 minutes.

At the end of the operation rinsing takes place with twice 2 ml of DMF, once 4ml of dichloromethane (DCM), once 2 ml of isopropanol and 6 times 2 ml of DMF.

b) Preparation of NH$_2$-Arg-Zaa'-R$^2$

In this stage, there is a cleaving of the FMOC group with 3 times 2.5 ml respectively for 5.5 and 10 minutes of a piperidine:DMF mixture (1.1). This operation is followed by rinsing twice with 2 ml of DMF, once with 4 ml of DCM, once with 2 ml of isopropanol and 6 times with 2 ml of DMF.

c) Preparation of Pheψ(PO(OR$^3$)CH$_2$)Xaa'-Arg-Zaa'-R$^2$, with Xaa'=Gly

For this stage use is made of synthone 1 obtained in example 1 and it is coupled with the product NH$_2$-Arg-Met-R$^2$ obtained in the preceding stage.

For said coupling use is made of 1.5 equivalent of synthone 1, 3 equivalents of HBTU, 4 equivalents of DIPEA and 1.5 ml of DMF, the reaction being performed for 60 minutes. This is followed by rinsing twice with 2 ml of DMF, once with 4 ml of DCM, once with 2 ml of isopropanol and 6 times with 2 ml of DMF.

d) Preparation of Z-Pheψ(PO(OR$^3$)CH$_2$)Xaa'-Arg-Zaa'OH

In this stage separation takes place of the peptide from the solid phase R$^2$, the cleaving being carried out with 5 ml of a mixture of acetic axid, trifluoroethanol (TFE) and DCM (2:2:6). Following 120 minutes of contact, rinsing takes place with 10 ml of DCM and drying takes place to dryness.

e) Preparation of peptide 1

In this stage the adamantyl group R$^3$ is eliminated by operating in the following way.

The peptide obtained in the preceding stage is contacted with 2.5 ml of a mixture containing 50 to 60% trifluoroacetic acid (TFA), 5% phenol, 5% water, 5% thioanisole, 2.5% ethane dithiol and 42.5 to 32.5% DCM, operating for a period of 40 to 180 minutes. This is followed by drying to dryness and treatment with 3 equivalents of sodium bicarbonate in 2 ml of water and the impurities are extracted in diethyl ether. The product obtained then undergoes lyophilization.

In the cleaving stage it is possible to use in place of the aforementioned mixture 2.5 ml of a mixture of 50 to 60% TFA, 5% water and 45 to 35% DCM.

Peptide 1 obtained has the following characteristics:

Rf=0.7 (propanol:water system 64:36), high performance liquid chromatography (HPLC): retention time 19.5 min, linear gradient of 28 min: eluent A (aqueous solution with 0.1% trifluoroacetic acid TFA) and eluent B (65% acetonitrile in aqueous solution with 0.1% TFA).

EXAMPLE 5

This example follows the same operating procedure as in example 4 for preparing peptides 2 to 21 given in the attached table 1.

EXAMPLE 6

In this example testing takes place of the biological activity of peptides 1 to 21 for determining their inhibiting effect with respect to the endopeptidase 24-15 and operating in the following way.

Incubation takes place for 1 hour at 37° C. of 2 nmole (20 µmole/l) of neurotensin, which is a known endopeptidase 24-15 substrate, with 7 µg of purified endopeptidase 24-15 in a final volume of 100 µl of tris-HCl buffer, 50 nM, pH 7.5, in the absence of an inhibitor (control) or in the presence of the peptide tested at concentrations from $10^{-11}$ to $10^{-7}$ mole/l. After 1 hour incubation analysis takes place of the solutions by HPLC. On the basis of this analysis the inhibition constant Ki of the tested peptide is determined.

The results obtained are given in table 1.

EXAMPLE 7

This example studies the inhibiting effect of the peptides of the invention with respect to endopeptidase 24-16.

To this end, incubation takes place for 1 hour at 30° C. of 2 nmole (20 µmole/l) of neurotensin, which is a known endopeptidase 24-16 substrate with 8 µg of endopeptidase 24-16 purified in a final volume of 100 µl of tris-HCl buffer, 50 mM, pH 7.5, in the absence of peptide (control) or in the presence of the peptide tested at concentrations from $10^{-11}$ to $10^{-7}$ mole/l. After 1 hour of incubation analysis takes place of the solutions by HPLC and the inhibition constant Ki of the tested peptide is determined.

The results obtained are given in table 1.

This table also gives the selectivity of the peptide relative to endopeptidase 24-16, namely the ratio $Ki_{24-16}/Ki_{24-15}$.

The results of table 1 show that very effective peptides are obtained, particularly when the final amino acid of the peptide is Met, Nle, Ala, Phe, Tyr, Leu or Gln.

Thus, with peptides 1 to 7, more effective inhibitors than the known inhibitor Cpp-Ala Pro-Phe-pAb are obtained, the latter having an inhibition constant of 7 nM with respect to endopeptidase 24-15 of the rat, as described by Dando et al in Biochem. J., 294, 1993, pp 451–457.

EXAMPLE 8

In this example preparation takes place of peptides of formula Z-Pheψ(PO$_2$CH$_2$)Ala-Lys-Zaa'OH following the operating procedure of example 4, but using synthone 2.

This is followed by the testing of the inhibiting effect of these peptides with respect to endopeptidase 24-15 and optionally endopeptidase 24-16 following the operating procedure of examples 6 and 7.

The results obtained are given in table 2. These results show that peptides 22 to 34 are very powerful endopeptidase 24-15 inhibitors.

For comparison purposes, it should be noted that mixtures of peptides of type Z-Pheψ(PO$_2$CH$_2$)Ala-Pro-Zaa'OH and Z-Pheψ(PO$_2$CH$_2$)Ala-Nle-Zaa'OH, compared with mixtures of type:

Z-Pheψ|PO$_2$CH$_2$|Ala Arg Zaa' or Z-Pheψ|PO$_2$CH$_2$|Ala-Lys Zaa' in which Zaa' represents 20 natural amino acids, have much lower inhibition constants Ki and also have a very low selectivity with respect to the inhibition of endopeptidase 24-16.

| PEPTIDE | K$_i$24-15 (nM) | K$_i$24-16 (nM) | SELECTIVITY |
|---|---|---|---|
| Z—Phe Ψ (PO$_2$CH$_2$)Ala—Pro—Zaa'OH | 35 | 60 | 1.7 |
| Z—Phe Ψ (PO$_2$CH$_2$)Ala—Nle—Zaa'OH | 52 | 330 | 6.3 |
| Z—Phe Ψ (PO$_2$CH$_2$)Ala—Lys—Zaa'OH | 3.5 | 900 | 257 |
| Z—Phe Ψ (PO$_2$CH$_2$)Ala—Arg—Zaa'OH | 3.5 | 1600 | 457 |

Thus, it can be seen that the replacement of Arg or Lys by Pro or Nle gives inhibitors which are no longer very selective with respect to endopeptidase 24-15.

EXAMPLE 9

In this example preparation takes place of peptides 42, 43 and 44 following the operating procedure of example 4, but starting with synthone 2 for peptides 42 and 43 and synthone 3 for peptide 44.

The inhibiting properties of the peptides obtained with respect to endopeptidase 24-15 and endopeptidase 24-16 are tested, adopting the operating procedure of examples 6 and 7. The results obtained are given in table 3.

This table also gives the results obtained with peptides 1, 4 and 25 having the same amino acid at the chain end as those of peptides 42, 43 and 44.

The table results show that peptide 43 Z-$_{(D-L)}$Pheψ(PO$_2$CH$_2$)$_{(D-L)}$Ala-Arg-PheOH is the most powerful inhibitor known for endopeptidase 24-15, whilst being extremely selective. The selectivity factor with respect to endopeptidase 24-16 is 3335. For example, the known inhibitor Cpp-Ala-Pro-Phe-pAb has a Ki of 7 nM relative to rat endopeptidase 24-15, whereas under the same conditions the mixture of inhibitors Z-$_{(D-L)}$Pheψ(PO$_2$CH$_2$)$_{(D-L)}$Ala-Arg-PheOH containing 4 diastereoisomers has a Ki of 0.16 nM. As it is a mixture, it can be expected that one of these diastereoisomers has a Ki of approximately 40 pM, namely an affinity difference with product Cpp-Ala-Pro-pAb of approximately 175. In the same way, peptide 42 Z-$_{(D-L)}$Pheψ(PO$_2$CH$_2$)$_{(D-L)}$Ala-Arg-MetOH constitutes the most powerful mixture of the tested peptides according to the invention with a Ki of 0.067 nM. One of the diastereoisomers of this mixture doubtless has an affinity of approximately 15 pM, namely a power increased by a factor of 440. In addition, all these peptides are very selective for endopeptidase 24-15.

Finally, it is important to note that the specificity between the endopeptidases 24-15 of different species (rat, chicken, man) do not vary, so that the peptides according to the invention are powerful inhibitors of endopeptidase 24-15 in man.

TABLE 1

| PEPTIDE | FORMULA | $K_i$ 24-15 (nM) | $K_i$ 24-16 (nM) | SELECTIVITY |
|---|---|---|---|---|
| No. 1 | Z—Phe Ψ (PO$_2$CH$_2$)Gly—Arg—Met | 0.35 | 132 | 377 |
| No. 2 | Z—Phe Ψ (PO$_2$CH$_2$)Gly—Arg—Nle | 1.6 | 213 | 135 |
| No. 3 | Z—Phe Ψ (PO$_2$CH$_2$)Gly—Arg—Ala | 2.2 | 201 | 91 |
| No. 4 | Z—Phe Ψ (PO$_2$CH$_2$)Gly—Arg—Phe | 2.7 | 1103 | 409 |
| No. 5 | Z—Phe Ψ (PO$_2$CH$_2$)Gly—Arg—Tyr | 3.6 | 596 | 165 |
| No. 6 | Z—Phe Ψ (PO$_2$CH$_2$)Gly—Arg—Leu | 5.0 | 846 | 169 |
| No. 7 | Z—Phe Ψ (PO$_2$CH$_2$)Gly—Arg—Gln | 6.1 | 690 | 113 |
| No. 8 | Z—Phe Ψ (PO$_2$CH$_2$)Gly—Arg—Val | 9.3 | 1128 | 121 |
| No. 9 | Z—Phe Ψ (PO$_2$CH$_2$)Gly—Arg—Ile | 9.6 | 589 | 61 |
| No. 10 | Z—Phe Ψ (PO$_2$CH$_2$)Gly—Arg—Trp | 13.1 | 2664 | 203 |
| No. 11 | Z—Phe Ψ (PO$_2$CH$_2$)Gly—Arg—Gly | 13.8 | 1661 | 120 |
| No. 12 | Z—Phe Ψ (PO$_2$CH$_2$)Gly—Arg—Arg | 14.0 | 2037 | 145 |
| No. 13 | Z—Phe Ψ (PO$_2$CH$_2$)Gly—Arg—Asn | 19.5 | 1380 | 71 |
| No. 14 | Z—Phe Ψ (PO$_2$CH$_2$)Gly—Arg—His | 23.2 | 3009 | 129 |
| No. 15 | Z—Phe Ψ (PO$_2$CH$_2$)Gly—Arg—Ser1 | 28.8 | 2057 | 87 |
| No. 16 | Z—Phe Ψ (PO$_2$CH$_2$)Gly—Arg—Ser2 | 32.0 | 1379 | 43 |
| No. 17 | Z—Phe Ψ (PO$_2$CH$_2$)Gly—Arg—Thr | 35.2 | 3636 | 103 |
| No. 18 | Z—Phe Ψ (PO$_2$CH$_2$)Gly—Arg—Lys | 138 | 25700 | 186 |
| No. 19 | Z—Phe Ψ (PO$_2$CH$_2$)Gly—Arg—Glu | 163 | 8149 | 50 |
| No. 20 | Z—Phe Ψ (PO$_2$CH$_2$)Gly—Arg—Asp | 352 | 20373 | 58 |
| No. 21 | Z—Phe Ψ (PO$_2$CH$_2$)Gly—Arg—Pro | 3520 | 36670 | 10 |

TABLE 2

| PEPTIDE | FORMULA | $K_i$ 24-15 (nM) | $K_i$ 24-16 (nM) | SELECTIVITY |
|---|---|---|---|---|
| No. 22 | Z—Phe Ψ (PO$_2$CH$_2$)Ala—Lys—Met | 0.115 | 225 | 1957 |
| No. 23 | Z—Phe Ψ (PO$_2$CH$_2$)Ala—Lys—Nle | 0.63 | 162 | 257 |
| No. 24 | Z—Phe Ψ (PO$_2$CH$_2$)Ala—Lys—Ala | 0.83 | 436 | 525 |
| No. 25 | Z—Phe Ψ (PO$_2$CH$_2$)Ala—Lys—Phe | 1.00 | 1652 | 1652 |
| No. 26 | Z—Phe Ψ (PO$_2$CH$_2$)Ala—Lys—Leu | 1.82 | 893 | 491 |
| No. 27 | Z—Phe Ψ (PO$_2$CH$_2$)Ala—Lys—Ile | 1.94 | 1265 | 652 |
| No. 28 | Z—Phe Ψ (PO$_2$CH$_2$)Ala—Lys—Gln | 2.18 | | |
| No. 29 | Z—Phe Ψ (PO$_2$CH$_2$)Ala—Lys—Tyr | 2.30 | | |
| No. 30 | Z—Phe Ψ (PO$_2$CH$_2$)Ala—Lys—Val | 2.60 | | |
| No. 31 | Z—Phe Ψ (PO$_2$CH$_2$)Ala—Lys—Arg | 3.17 | | |
| No. 32 | Z—Phe Ψ (PO$_2$CH$_2$)Ala—Lys—Asn | 4.90 | | |
| No. 33 | Z—Phe Ψ (PO$_2$CH$_2$)Ala—Lys—Gly | 5.10 | | |
| No. 34 | Z—Phe Ψ (PO$_2$CH$_2$)Ala—Lys—Trp | 5.78 | | |
| No. 35 | Z—Phe Ψ (PO$_2$CH$_2$)Ala—Lys—His | 7.13 | | |
| No. 36 | Z—Phe Ψ (PO$_2$CH$_2$)Ala—Lys—Thr | 10.1 | | |
| No. 37 | Z—Phe Ψ (PO$_2$CH$_2$)Ala—Lys—Ser | 11.9 | | |
| No. 38 | Z—Phe Ψ (PO$_2$CH$_2$)ASla—Lys—Lys | 26.9 | | |
| No. 39 | Z—Phe Ψ (PO$_2$CH$_2$)Ala—Lys—Glu | 53.5 | | |
| No. 40 | Z—Phe Ψ (PO$_2$CH$_2$)Ala—Lys—Asp | 109.0 | | |
| No. 41 | Z—Phe Ψ (PO$_2$CH$_2$)Ala—Lys—Pro | 1030 | | |

TABLE 3

| PEPTIDE | FORMULA | $K_i$ 24-15 (nM) | $K_i$ 24-16 (nM) | SELECTIVITY |
|---|---|---|---|---|
| No. 42 | Z—Phe Ψ (PO$_2$CH$_2$)Ala—Arg—Met | 0.067 | 88 | 1312 |
| No. 1 | Z—Phe Ψ (PO$_2$CH$_2$)Gly—Arg—Met | 0.35 | 132 | 377 |
| No. 43 | Z—Phe Ψ (PO$_2$CH$_2$)Ala—Arg—Phe | 0.158 | 527 | 3335 |
| No. 4 | Z—Phe Ψ (PO$_2$CH$_2$)Gly—Arg—Phe | 2.7 | 1103 | 409 |
| No. 44 | Z—Phe Ψ (PO$_2$CH$_2$)Leu—Arg—Phe | 14 | 2285 | 164 |
| No. 25 | Z—Phe Ψ (PO$_2$CH$_2$)Ala—Lys—Phe | 1 | 1652 | 1652 |

We claim:

1. Peptide derivative according to the formula:

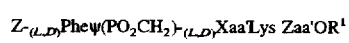

(II)

in which

Z represents the benzyloxycarbonyl group,

ψ(PO$_2$CH$_2$) indicates that the peptide bond (CO—NH) has been replaced by the phosphine bond (PO$_2$—CH$_2$).

Xaa' represents Gly, Ala or Leu,

Zaa' represents Met, Nle, Phe, Leu or Ile, and $R^1$ represents a hydrogen atom, $NH_4^+$ or a pharmaceutically acceptable metal.

2. Peptide derivative according to claim 1, characterized in that Xaa' represents Ala, Zaa' represents Met and $R^1$ represents a hydrogen atom.

3. Peptide derivative of formula

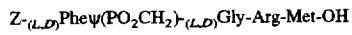

in which Z represents the benzyloxycarbonyl group and ψ($PO_2CH_2$) indicates that the peptide bond (CO—NH) has been replaced by the phosphine bond ($PO_2$—$CH_2$).

4. Peptide derivative of formula

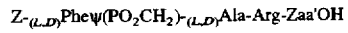

in which

Z represents the benzyloxycarbonyl group,

ψ($PO_2CH_2$) indicates that the peptide bond (CO—NH) has been replaced by the phosphine bond ($PO_2CH_2$) and Zaa' represents Met or Phe.

5. A pharmaceutical composition which inhibits endopeptidase 24-15, consisting essentially of a pharmaceutically effective quantity of a peptide derivative having the formula:

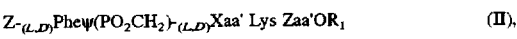 (II), or

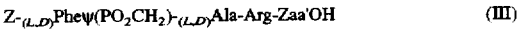 (III)

wherein

Z represents a benzyloxycarbonyl group;

Pheψ($PO_2CH_2$) indicates that the peptide bond (CO—NH) has been replaced by the phosphine bond ($PO_2CH_2$);

Xaa' represents Gly, Ala or Leu;

Zaa' represents Met, Nle, Phe, Leu or Ile in formula (II), and Met or Phe in formula (III); and $R^1$ represents a hydrogen atom, $NH_4^+$ or a pharmaceutically acceptable metal.

6. The pharmaceutical composition of claim 5, wherein the polypeptide derivative is a polypeptide derivative of formula (II) with Xaa' representing Ala, Zaa' representing Met and $R^1$ representing a hydrogen atom.

* * * * *